United States Patent [19]

Werschmidt et al.

[11] Patent Number: 5,782,816
[45] Date of Patent: Jul. 21, 1998

[54] BI-DIRECTIONAL VALVE AND METHOD OF USING SAME

[75] Inventors: Gary S. Werschmidt, Yorba Linda; Raymond P. Feith, Rialto, both of Calif.; David R. Kipp, 2371 Edna Way, Upland, Calif. 91784

[73] Assignee: David R. Kipp, Upland, Calif.

[21] Appl. No.: 525,837

[22] Filed: Sep. 7, 1995

[51] Int. Cl.⁶ ............................................ A61M 5/00
[52] U.S. Cl. .................... 604/256; 604/83; 604/283; 137/903; 251/149.6; 251/149.7
[58] Field of Search .................. 604/181–3, 202, 604/236, 246, 249, 250, 256–7, 283, 905, 83; 137/903; 251/149.6, 149.7

[56] References Cited

U.S. PATENT DOCUMENTS

| | | | |
|---|---|---|---|
| 4,723,694 | 2/1988 | Sykes | 137/903 |
| 4,798,226 | 1/1989 | Struth | 137/903 |
| 5,031,675 | 7/1991 | Lindgren | 604/905 |
| 5,061,253 | 10/1991 | Yoshida | 604/246 |
| 5,085,645 | 2/1992 | Purdy et al. | 604/256 |
| 5,509,433 | 4/1996 | Paradis | 604/249 |
| 5,535,785 | 7/1996 | Werge et al. | 604/249 |
| 5,569,235 | 10/1996 | Ross et al. | 604/249 |

Primary Examiner—Mark Bockelman
Attorney, Agent, or Firm—Richard L. Myers

[57] ABSTRACT

A connector adapted to facilitate medicinal access into an intravenous tube includes a housing having a base and a cap defining a channel through the housing. A valve element disposed in the channel includes a plug and elastomeric shaft which biases the plug into sealing engagement with the housing. Operation of the connector by inserting a male Luer fitting in the housing axially compresses the valve element to a canted position thereby permitting medicinal access through the channel and into the intravenous tube. Canting of the valve element can be facilitated by providing a finger along the channel or by providing a predetermined buckling section along the valve element. The shaft of the valve element can be rounded and disposed in an arcuate cavity of the housing to further facilitate canting of the valve element.

24 Claims, 5 Drawing Sheets

BI-DIRECTIONAL VALVE AND METHOD OF USING SAME

BACKGROUND OF THE INVENTION

1. Field of the Invention

This invention relates generally to fluid delivery devices and more specifically to valves, access parts, and other connectors for use in introducing medication and fluids into a patient and for removing fluids from the patient.

2. Description of the Prior Art

When it is contemplated that a patient will require multiple injections into the vascular system, an intravenous tubing set is commonly used. This set will typically include a primary needle or catheter which provides access to the vascular system, and a connector which is coupled to the needle through tubing. This connector can be repeatedly accessed by a medication delivery apparatus, such as a syringe, having a secondary needle. With this tubing set, the trauma to the patient is reduced to a single puncture of the vascular system by the primary needle. Repeated use of the secondary needle for introducing fluids into the connector does not result in additional trauma to the patient.

In some cases, the connector forms an injection site, a PRN adapter, or PRN extension set in which case the medication is added to a constant flow of nutrients or other intravenous solutions through the connector. In such applications, the intravenous solution flows from an elevated container through the connector and into the primary needle. Medications are typically added to this intravenous solution at the connector.

These types of connectors generally include a sealed entry port which communicates through the tubing and the needle into the vascular system of the patient. This sealed entry port is typically constructed of a latex plug sometimes referred to as a septum. Medication is introduced into the connector by penetrating the septum with the secondary needle. The latex septum is self-sealing such that the needle hole created in the septum automatically closes when the secondary needle is removed.

A major drawback of this conventional practice is associated with use of the secondary needle to puncture the septum. Once this needle is exposed to the patient's body fluids, within a distance of 36" from the insertion site, the injection is considered high risk, and the contaminated needle threatens the health care workers with disease and other life-threatening injuries.

Several devices have been developed which provide for secondary access without the use of the secondary needle. Representative of these devices in the apparatus disclosed is U.S. Pat. No. 5,242,432 issued to DeFrank which discloses a safety valve for introducing medication into a patient. Although such devices may eliminate the risk of secondary needle stick, they present other risks which relate to the pooling of fluid on or around external surfaces. Ideally, a connector or other access device should not promote pooling during the ordinary course of its use due to the potential for bacterial infection. If a reservoir or cavity is created and not cleaned, bacteria may develop in the reservoir. That bacteria could find its way into the patient's bloodstream while either administering fluids to the patient or removing the fluids from the patient.

SUMMARY OF THE INVENTION

These deficiencies of the prior art are overcome with the present invention which comprises a needleless access device which is inexpensive to manufacture, disposable and easily adaptable for use in various medical applications. This device eliminates the need for a secondary needle because it is easily connectable to intravenous administration sets and other standard medical fittings without the need for accessory components such as needles or blunt cannulas. It is simple in design and easy to disinfect, while offering a low cost of manufacture and high reliability.

The connector includes a housing which is typically formed with a base and a cap which define an interior channel that extends through the housing. A valve element, typically including a plug and a shaft is disposed along the channel. In a first natural position, the plug seals the channel. However, the plug is movable to a second position, typically by insertion of a male Luer fitting, in order to create the channel. In the second position, the valve element is canted off axis to open the channel and permit the administration of medication and other liquids into the patient's vascular system. In this canted position, a fluid path occurs along the channel between the top surface of the valve element and the interior of the housing.

The housing of the connector is free of any recesses or external crevices which might promote pooling or otherwise harbor microbes. The valve element and the housing form a substantially flat proximal surface which is easily wipeable, swabable or otherwise cleanable to disinfect the connector. Thus the connector can be decontaminated without requiring a separate cap which would otherwise elevate the cost of the device and complicate its use. The connector is easily activated by insertion of a male Luer fitting which is commonly used in tubing connections associated with intravenous delivery systems.

In one aspect of the invention, a connector is adapted to facilitate bidirectional flow between a male fitting and a receptacle. The connector includes a housing having an axis extending between a proximal end and a distal end which is attached to the intravenous tube. Portions of the housing define a valve seat at its proximal end. A valve element is disposed in the housing and has a second axis. The valve element is movable by insertion of the male Luer fitting into the housing from a first position to a second position. In the first position the valve element forms with a seal with the valve seat of the housing. The valve element in the second position is disposed with the second axis of the valve element displaced from the first axis of the housing to form a fluid channel from the male Luer fitting to the receptacle.

In a further aspect of the invention, the housing has a proximal surface at its proximal end. The valve element has a proximal surface which has a substantially planar relationship with the proximal surface of the housing to facilitate antiseptic wiping at the proximal end of the connector.

In a further aspect of the invention, the connector is adapted to facilitate access into an intravenous tube. The connector includes a housing and a valve element disposed in the housing to define with the housing a fluid channel extending between the proximal end and the distal end of the housing. The valve element has a second axis which is movable between a first position wherein the axis of the housing is aligned with the axis of the valve element to close the fluid channel and a second position wherein the axis of the valve element is displaced from the axis of the housing to open the fluid channel.

In still a further aspect of the invention, a connector is adapted to facilitate medicinal access to an intravenous tube. The connector includes a housing having a channel extending therethrough. A base forms a portion of the housing as

3 does a cap which has a fixed relationship with the base. A valve element disposed in the channel of the housing includes a plug and a shaft having properties for biasing the plug into sealing engagement with the housing to seal the channel in a first position of the valve element, and for being axially compressed to displace the plug from the housing and open the channel.

A method associated with the invention relates to operation of the connector when it is disposed between a male fitting and a receptacle. The method includes the steps of providing a housing having a channel, and an axis extending between a proximal end and a distal end. A valve element is positioned within the channel and biased to close the channel. The receptacle is coupled to the distal end of the housing while the male fitting is positioned to engage the valve element at the proximal end of the housing. In accordance with the method the male fitting is moved generally parallel to the axis of the housing to open the channel between the male fitting and the receptacle.

These and other features and advantages of the invention will become more apparent with a discussion of preferred embodiments and best mode of the invention, and reference to the associated drawings.

DESCRIPTION OF THE DRAWINGS

FIG. 12 is an axial cross section view of still a further embodiment of the connector having a valve element with a hollow shaft;

FIG. 13 is an axial cross section view of a further embodiment of the invention wherein the shaft of the valve

4 element is sculpted to facilitate priming and provide a more predictable canting configuration and flow rate; and FIG. 14 is a radial cross section view taken along lines 14—14 of FIG. 13.

DESCRIPTION OF PREFERRED EMBODIMENTS AND BEST MODE OF THE INVENTION

Figure 1:
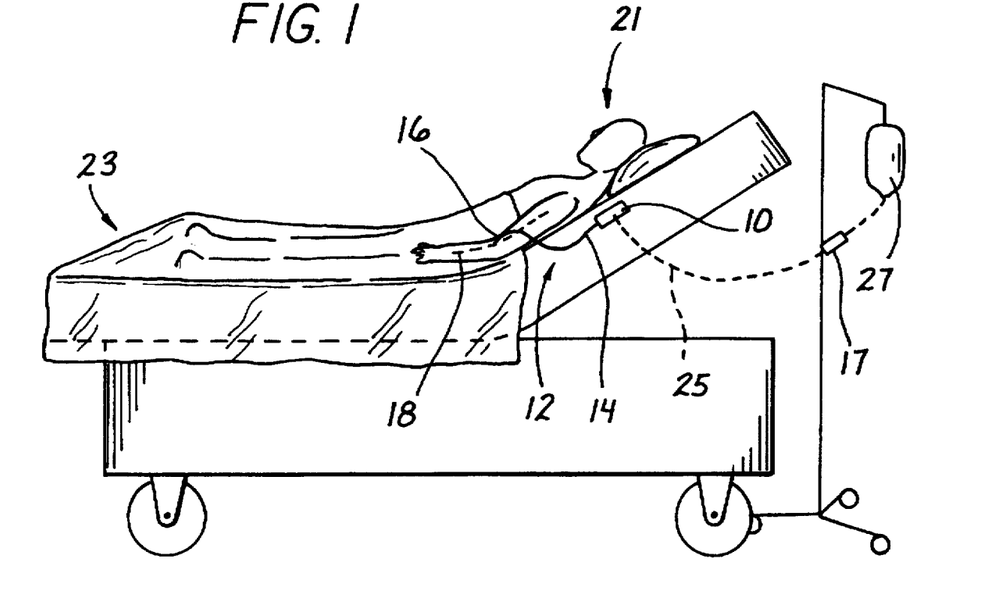
FIG. 1 is a side elevation view of a patient lying on a bed and connected to an intravenous tubing set including a connector associated with the present invention.

A connector is illustrated in FIG. 1 and designated generally by the reference numeral 10. The connector 10 forms part of an intravenous tubing set 12 comprising a length of tubing 14, and a primary needle 16. The tubing set 12 is commonly used to facilitate connection to an IV line which may have a Y-site connector 17 for the injection of fluids and medications into a vein 18 of a patient 21. In FIG. 1, the patient 21 is illustrated in a generally prone position on a hospital bed 23.

Repeated injections of medications or other fluids can be administered with multiple needle sticks directly into the vein 18 of the patient 21. However, each needle stick would be accompanied by trauma to the patient 21. The tubing set 12 reduces this trauma by requiring only a single stick with the primary needle 16. Then the remaining secondary needle sticks can be made through the connector 10 which accesses the vein 18 through the tubing 14. These secondary needle sticks into the connector 10 avoid trauma to the patient 21.

In some cases, the connector 10 forms a "T"-site or a "Y"-site. In these cases, the connector 10 is also coupled to tubing 25 which communicates with an elevated bottle 27 containing various intravenous solutions. As the solution from the bottle 27 continuously drips into the tubing 25, it flows through the connector 10, the tubing 14 and the needle 16 into the vein 18. Additional medications can be inserted through a secondary channel in the connector 10. The tubing 25 is dotted in FIG. 1 to indicate that the connector 10 may function as a single access site or as a "T"-site or "Y"-site connector 17.

Figure 2:
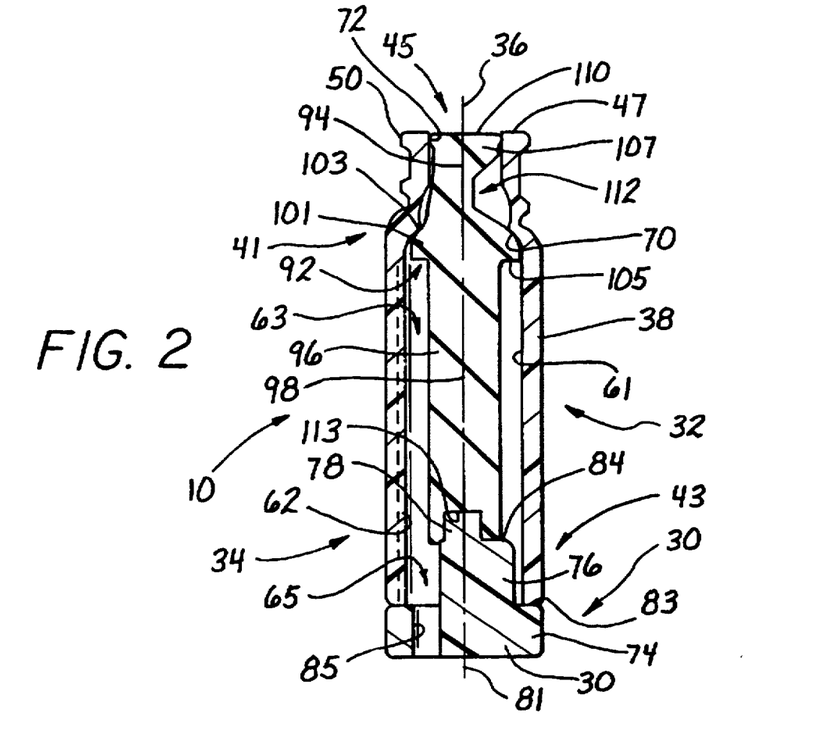
FIG. 2 is an axial cross-section view illustrating a preferred embodiment of the connector disposed in a normal closed state.

A preferred embodiment of the connector 10 is illustrated in FIG. 2 and includes a base 30, and cap 32 which together form a housing 34 which extends generally along an axis 36. The cap 32 is elongate in configuration and includes a wall 38 which extends between a proximal end 41 and a distal end 43. At the proximal end 41, the wall 38 narrows to form an opening 45 at a proximal surface 47. The wall 38 can be provided with external threads 50 which form, in a preferred embodiment, a female Luer fitting.

The wall 38 of the cap 32 has an inner surface 61 which defines a channel 63 that extends through the housing 34 to a distal opening 65. At the proximal end 41, the inner surface 61 forms an annular shoulder which functions as a primary valve seat 70 best illustrated in FIG. 2. In proximity to the proximal surface 47, the inner surface 61 forms a secondary valve seat 72 which has a more cylindrical configuration. One or more longitudinal slots 62 can be formed in the wall 38 to define the channel 63 outwardly of the surface 61.

The base 30 of the housing 34 can be provided in a variety of forms as described in greater detail below. In the embodiment of FIG. 2, the base 30 is formed as a plurality of concentric cylinders 74, 76 and 78 which are stacked along an axis 81 that is concentric with the axis 36 in this embodiment. The bottom cylinder 74 has a diameter which is generally equivalent to the outside diameter of the cap 32.

A shoulder 83 is formed where the bottom cylinder 74 meets the intermediate cylinder 76. This intermediate cylinder 76 is preferably provided with an outside diameter substantially equivalent to the inside diameter of the surface 61. This enables the base 30 to be force fit into the distal end 43 of the cap 32, with the cap 32 resting on the shoulder 83 in abutting relationship with the cylinder 74.

Interiorly of the channel 63, the top cylinder 78 forms a post which extends proximally of the intermediate cylinder 76. A shoulder 84 is formed where the intermediate cylinder 76 meets the top cylinder 78. The base 30 is suitably apertured, typically by forming a longitudinal hole 85 in the intermediate cylinder 76 and the bottom cylinder 74, in order to extend the channel 63 through the distal end of the housing 34.

Of particular interest to the present invention is a valve element 90 which is disposed interiorly of the housing 34 and has a generally elongate configuration in the embodiment of FIG. 2. This valve element 90 may be formed totally or partially of elastomeric materials to facilitate the deflection and sealing characteristics desired for a particular embodiment of the connector 10. The valve element 90 in the illustrated embodiment includes a plug 92 which is disposed along an axis 94 and a shaft 96 extending from the plug 92 along an axis 98. In the illustrated embodiment the valve element 90 is coaxial with the housing 34. Accordingly, the various axes 36, 94, 98 and 81 are collinear in this embodiment.

The plug 92 formed at the proximal end 41 of the valve element 90 includes a flange 101 having a proximal surface 103 and a distal surface 105. Proximally of the flange 101, the plug 92 has a generally conical configuration and extends to a nose 107 having a proximal surface 110. Between the proximal surface 110 and the surface 105 associated with the flange 101, the plug 92 is provided with a buckling section at a predetermined location laterally of the axis 94. In the illustrated embodiment this buckling section takes the form of a notch 112.

The valve element 90 is of particular interest to the present invention as it is the operation of this element 90 which enables the connector 10 to provide for a closed, sealed condition in one operative state, and to provide for an actuated open condition in a second operative state. The closed state is illustrated in FIG. 2 where the proximal surface 110 has a first angle (such as 90 degrees) to the axis 36; the open state is illustrated in FIG. 3 where the proximal surface 110 has a second angle (less than the first angle) to the axis 36.

In the closed state, the valve element 90 is generally in a natural condition and is self-biased to substantially its maximum length. In this closed state, the plug 92 associated with the element 90 is biased into sealing engagement with the inner surface 61 of the cap 32. More specifically, the surface 103 of the flange 101 is pressed into sealing engagement with the primary valve seat 70 to form a primary seal between the cap 32 and the plug 92. In the closed state, a secondary seal is also formed between the circumferential surface of the nose 107 and the inner surface 61 which defines the opening 45. For reasons discussed in greater below, the proximal surface 110 of the valve element 90 is in a substantially planar orientation with the proximal surface 47 when the valve element 90 is in the closed state.

In the illustrated embodiment, the valve 90 is provided with an axial bore 113 at its distal end. This bore is sized and configured to receive the post associated with the cylinder 74 of the base 30. In this embodiment, the distal end of the valve element 90 has a generally fixed relationship with the housing 34. This is in contradistinction to the proximal end of the valve element 90 which is generally free to move, at least axially, relative to the housing 34.

Figures 3, 4, 5:
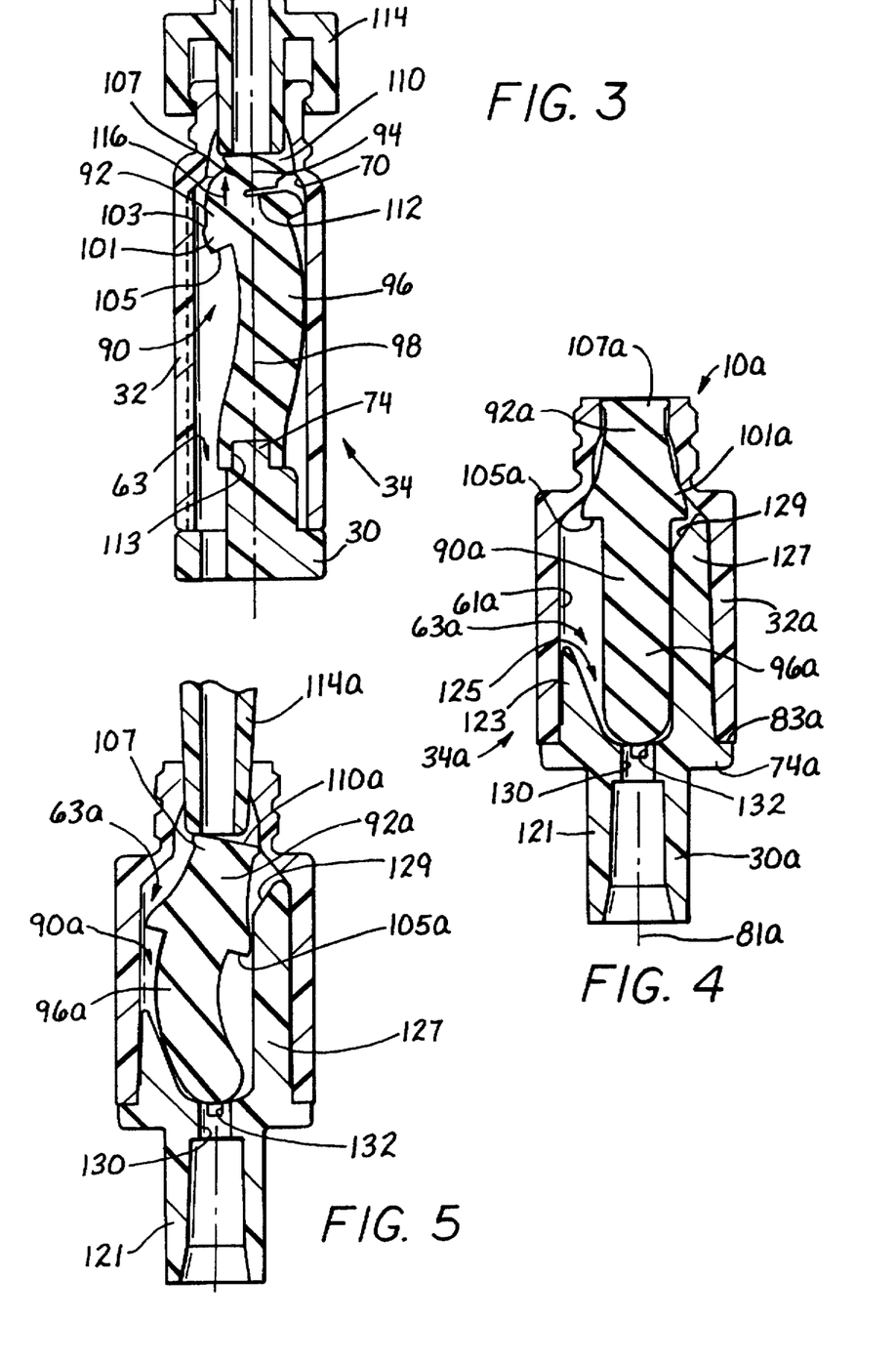
FIG. 3 is a side elevation view of the connector illustrated in FIG. 1, the connector being actuated by a male Luer fitting and being disposed in an activated open state.
FIG. 4 is an axial cross-section view of a further embodiment of the connector providing for a deflection finger and having a spherical base to promote canting of a valve element.
FIG. 5 is an axial cross-section view of the connector illustrated in FIG. 4, the connector shown in its activated open state.

As illustrated in FIG. 3, the open state of the connector 10 is achieved by compressing the valve element 90 generally along its axes 94, 98. It will first be noted that this compression is achieved in a preferred embodiment by connecting a common male Luer fitting 114 to the female Luer fitting 52 associated with the cap 32. By providing the connector 10 with characteristics for being actuated by a common Luer fitting 114, the possibility of a needle stick with a secondary needle is totally avoided. In FIG. 3, the valve element 90 is compressed along its axis 94, 98. As used herein, the word "compress" and its derivatives refers to any position wherein the two ends of an elongate element are brought closer together. This may occur due to a shortening of the element along its axial length or due to a bending of the element off-axis which may or may not be accompanied with a shortening in the length of the element.

As the male Luer fitting 114 is inserted into the opening 45, it initially contacts the surface 110 of the valve element 90. Further insertion of the fitting 114 places an axial load on the valve element 90 which is felt in both the plug 92 and the shaft 96. In a preferred embodiment, this compressive force operates initially to break the secondary seal between the nose 107 and the housing 34, and then to compress the plug 92 primarily at the buckling section formed by the notch 112.

As the plug 92 collapses at the notch 112, it compresses along that side of the valve element 90 causing the proximal surface 110 to dip in the area of the notch 112. This effectively moves the area of contact between the Luer fitting 114 and the surface 110 away from the axis 94 and toward the side of the plug 92 opposite the notch 112. This area of contact is illustrated in FIG. 3 by an arrow 116 which is displaced from the axis 94.

As the notch 112 collapses, the additional force applied by insertion of the fitting 114 also operates to axially compress the shaft 96. With the compression of the valve element 90, the shaft 96 tends to cant, buckle, bow or otherwise bend toward the side of the axis 98 opposite the arrow 116. This compression of the shaft 96 tends to break the primary seal formed between the surface 103 of the plug 92 and the valve seat 70 of the cap 32. Having broken both the primary seal associated with the primary valve seat 70, and the secondary seal associated with the nose 107, the channel 63 is now opened to receive medication or other liquids through the Luer fitting 114 and the housing 34. Within the housing 34, this channel 63 is defined between the surface 61 of the cap and the outer surface of the valve element 90.

In further embodiments of the invention, elements of structure which are similar to those previously discussed will be designated by the same referenced numeral followed by a lower case letter associated with that embodiment. Accordingly, the embodiment of FIG. 4 includes the cap 32a and the base 30a which together form the housing 34a. The valve element 90a includes the plug 92a and the shaft 96a. This embodiment of the connector 10a differs from that previously discussed primarily in the structural configuration of the base 30a and the complimentary configuration associated with the distal end of the valve element 90a.

In the embodiment of FIG. 4, the base 30a includes the cylinder 74a and the associated shoulder 83a. Extending distally from the cylinder 74a, however, is a cylindrical fitting 121 which is sized and configured to receive the tubing 14 (FIG. 1). Proximally of the cylinder 74a, the base 30a is formed with a cylindrical structure 123 which has an outer surface 125 and defines a rounded cavity. The outer surface has an outside diameter which is substantially equivalent to the inside diameter of the surface 61. This facilitates sealing engagement between the cap 32a and the base 30a in the manner previously discussed. Upstanding from the cylindrical structure 123 is a finger or post 127 which extends into proximity with the plug 92a of the valve element 90a. In this particular embodiment, the finger 127 has a surface 129 which is disposed distally of the surface 105a of the flange 101a and which is inclined generally toward the plug 92a.

The closed state of this connector 110a is illustrated in FIG. 4 where the primary seal is formed by the flange 101a, and a secondary seal is formed by the nose 107a. The valve element 90a in this embodiment differs from that previously discussed in that there is no area of predetermined buckling, such as the notch 112 of the FIG. 2 embodiment. Additionally, there is no post 74 associated with the base 30a, but rather the valve element 90 is provided with a rounded configuration at the distal end of the shaft 96a. This rounded end of the shaft 96a seats (with a reduced radius of curvature) within the arcuate spherical recess 125 provided in the base 30a.

The channel 63a in the embodiment of FIG. 4 also differs from that previously discussed, primarily in the vicinity of the base 30a. In the illustrated embodiment, the base 30a is apertured along the axis 81a to form a hole 130. This hole 130 communicates with slots 132 and functions primarily to seat the hemispherical end of the shaft 96a along the axis 81a. The slots 132 provide access to the hole 130 radially outwardly of the shaft 96a to provide communication for the channel 63a between the cap 32a and the base 30a.

The connector 10a is illustrated in FIG. 4 in its natural closed state, and in FIG. 5 in its activated, open state. Once again, activation of the connector 10a is preferably accomplished with the male Luer fitting 114a. Insertion of this fitting against the proximal surface 110a of the plug 92a operates to axially compress the valve element 90a. In the absence of the notch 112 however, the fitting 114a tends to compress the element 90a axially until the distally facing surface 105a of the plug 92a contacts the surface 129 associated with the finger 127. At this point further axial compression by the fitting 114a forces the plug 92a slide along the surface 129 and to cant toward the finger 127. This causes the shaft 96a to cant away from the finger 127. The resulting portion of the element 90a illustrated in FIG. 5. The hemispherical shape of the shaft 96a facilitates rotation of its distal end within the arcuate recess 125 of the base 30a. It will be noted that in this embodiment the distal end of the shaft 96a is not axially fixed as was the case with the embodiment of FIG. 3. In general, this provides the advantage of a shorter shaft 96a and a commensurately shorter connector 10a.

With the valve element canted as illustrated in FIG. 5, the channel 63a extends through the Luer fitting 114a and along side the valve element 90a interiorly of the housing 34a. In the base 30a, the channel 63a extends into the slots 132 and the hole 130 to exit the connector 10a through the fitting 121.

Figures 6, 7, 8:
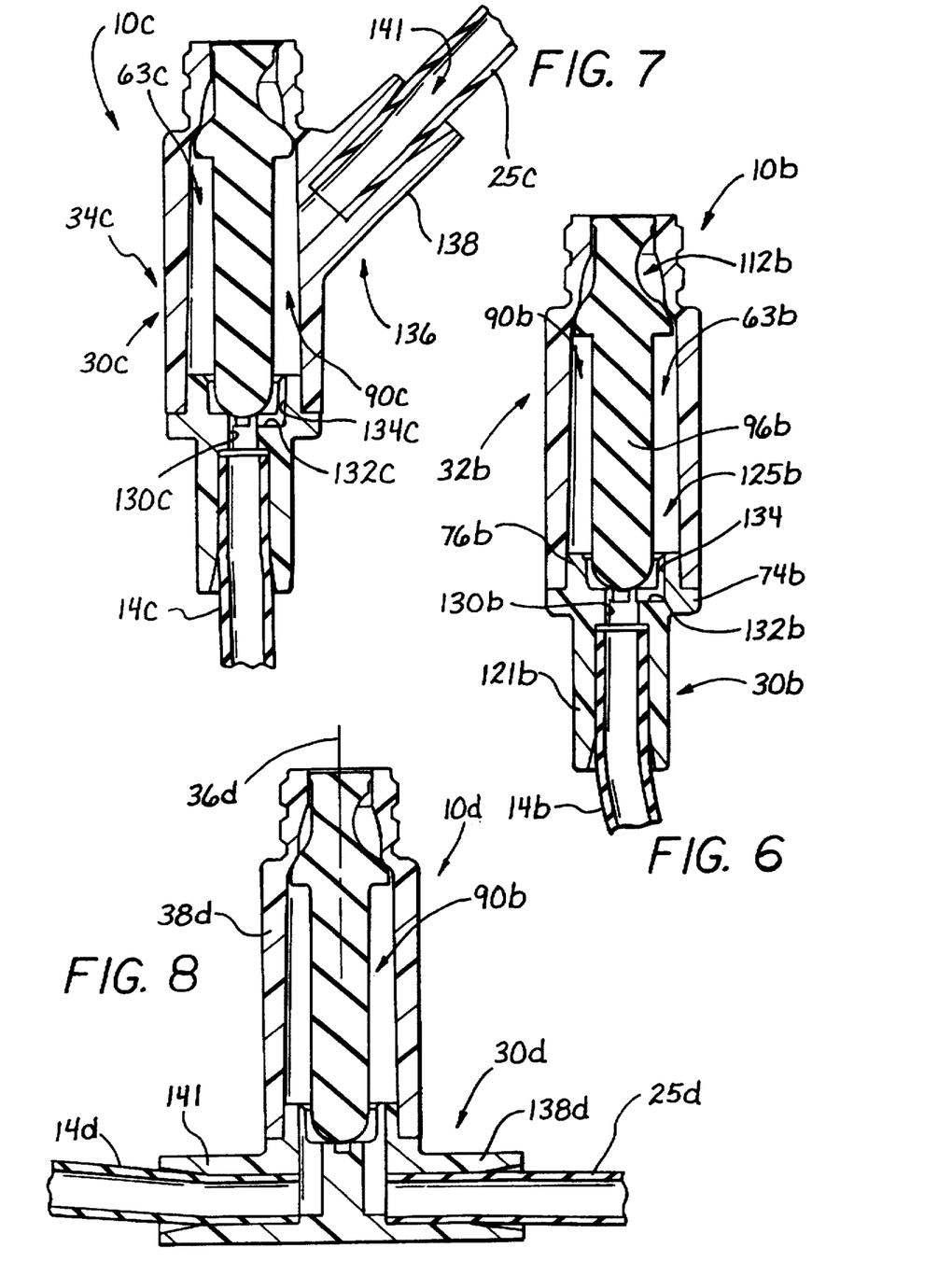
FIG. 6 is an axial cross-section view illustrating a further embodiment of the connector which is attached through a base to tubing.
FIG. 7 is an axial cross-section view of a further embodiment of the connector providing for a "Y"-site connection.
FIG. 8 is an axial cross-section view of an additional embodiment of the connector, this connector being similar to that of FIG. 6 but providing for a "T"-site connection.

A further embodiment of the invention is illustrated in FIG. 6 where the connector is designated by the reference numeral 10b. This embodiment is similar to that discussed with reference to FIG. 2 in that it includes the notch 112b. It is similar to the embodiment of FIG. 4 in that the shaft 96b is provided with a hemispherical distal end. The base 30b is also similar to that illustrated in of FIG. 4 in that it includes the fitting 121b and it provides a recess 125b to receive the distal end of the shaft 96b. This embodiment of the base 30b is similar to that discussed in FIG. 1 in that it includes the cylinder 76b in proximity to the cylinder 74b. In this particular embodiment, however, the cylinder 76b is radially apertured to form a slot 134 outwardly of the shaft 96b. This slot 134 communicates with the channel 63b interiorly of the cap 32b as well as the radial slot 132b and hole 130b associated with the base 30b. Deflection of the valve element 90b in response to insertion of the Luer fitting 114 is accomplished generally as described with reference to FIG. 3. However, the hemispherical distal end of the valve element 90b facilitates its canted orientation.

In the embodiment of FIG. 7, the connector 10c is similar to that of FIG. 6 except for the provision of a "Y"-site designated generally by the reference numeral 136. In this case, the cap 30c includes a fitting 138 which is sized and configured to receive the tubing 25c previously discussed with reference to FIG. 1. Thus the connector 10c is a "Y"-site connector which includes a primary channel 141 which extends through the tubing 25c, the fitting 138, interiorly of the housing 34c, and through the slots 132c, 134c and the hole 130c into the tubing 14c. It will be noted that this channel 141 is continuously open and unaffected by the disposition of the valve element 90c. When the valve element 90c is axially compressed, however, the channel 63c communicates with the channel 141 and permits the introduction of medication or other liquids into the tubing 14c.

A "T"-site connector 10d is illustrated in FIG. 7. The base 30d and valve element 90d are similar to those previously discussed but the base 30d differs considerably. In this embodiment, the fitting 138d which is configured to receive the tubing 25d is formed as part of the base 30d. A similar fitting 141 is provided to extend generally in the opposite direction from the fitting 138d and is sized and configured to receive the tubing 14d. With this configuration, the tubing 14d and 25d are generally collinear, while the axis 36d associated with the housing 34d is generally perpendicular to the tubing 14d, 25d.

Figures 9, 10:
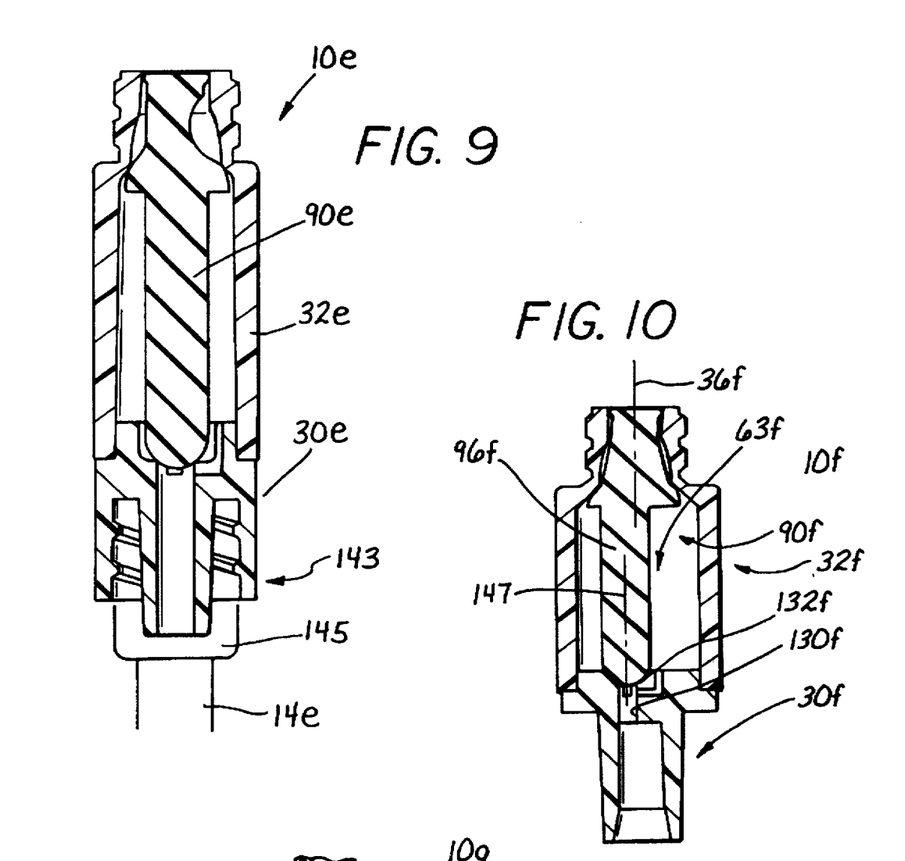
FIG. 9 is an axial cross-section view of a further embodiment of the connector having a base which forms a male Luer fitting.
FIG. 10 is an axial cross-section view of an additional embodiment of the connector including a housing and a valve element with a shaft in a normal state, the shaft being displaced off-axis with respect to the housing of the connector.

The connector 10e illustrated in FIG. 9 includes a cap 32e and valve element 90e which can be similar to any of the embodiments previously discussed. In this case however, the base 30e is provided in the form of a male Luer fitting 143 making it particularly adapted for connection to tubing, such as the tubing 14e, which terminates in a female Luer fitting 145.

The connector 10f illustrated in FIG. 10 includes a cap 32f which is generally symmetrical about an axis 36f. However, in this embodiment the valve element 90f is generally asymmetrical. Although the plug 92f in this embodiment can be coaxial with the housing 32f, the shaft 96f is preferably disposed along an axis 147 which is non-aligned with the axis 36f of the housing 32f. This configuration for the valve element 90f is advantageous in that a force applied along the axis 36f is not applied along the axis 147 associated with the shaft 96f. This tends to cause the shaft 96f to cant or buckle in the manner previously disclosed in order to open the channel 63f and facilitate the introduction of medication. In order to accommodate the off-axis orientation of the shaft 96a, a base 30f is formed with a hole 130f and slots 132f which are similarly to those described in FIG. 6. However in this embodiment, the hole 130f and slots 132f are similarly offset for disposition relative to the axis 147. Thus, even though the shaft 96f is offset from the axis 36f, it is nevertheless symmetrically disposed with reference to the hole 130f and slots 132f in the manner previously described with reference to FIG. 6.

Figure 11:
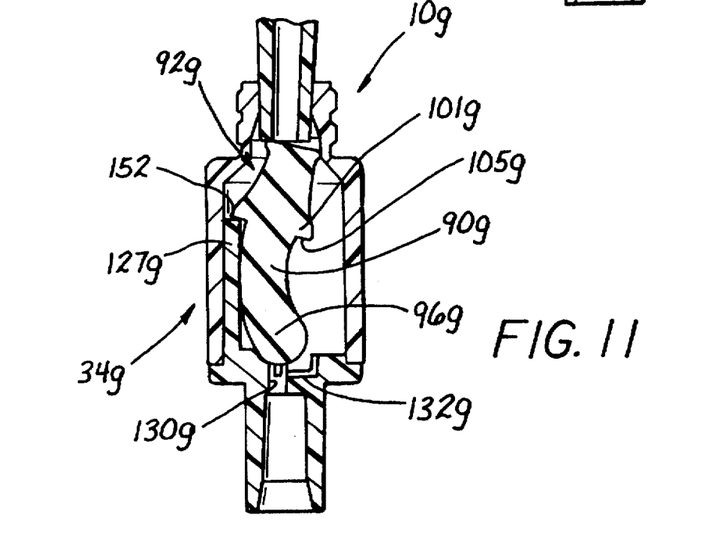
FIG. 11 is an axial cross section view of a further embodiment of the connector showing a valve element canted to an open state.

The connector 10g illustrated in FIG. 11 is similar to the connector 10a illustrated in FIGS. 4 and 5 in that it also includes a finger 127g. However, in the earlier embodiment, the finger 127 was provided with the surface 129 which faced proximally and radially toward the valve element 90. In FIG. 11, the finger 127g includes a surface 152 which faces proximally, but in this embodiment the surface 152 does not face toward the valve element 90g. As a consequence, the distally facing surface 105g associated with the plug 92g tends to engage and pivot on the surface 152 associated with the finger 127g. Rather than permitting these two surfaces to slide against each other, as was the case with the FIG. 4 embodiment, their engagement in the embodiment of FIG. 11 causes the valve element 90g to cant in the opposite direction. Thus, the plug 90g tilts away from the finger 127g while the shaft 96g bends toward the finger 127g. With this distinction, both of the embodiments of FIGS. 4 and 11 function to open and close the respective connectors 10a and 10g when the valve element 90 is axially compressed within the housing 34.

Figures 12, 13, 14:
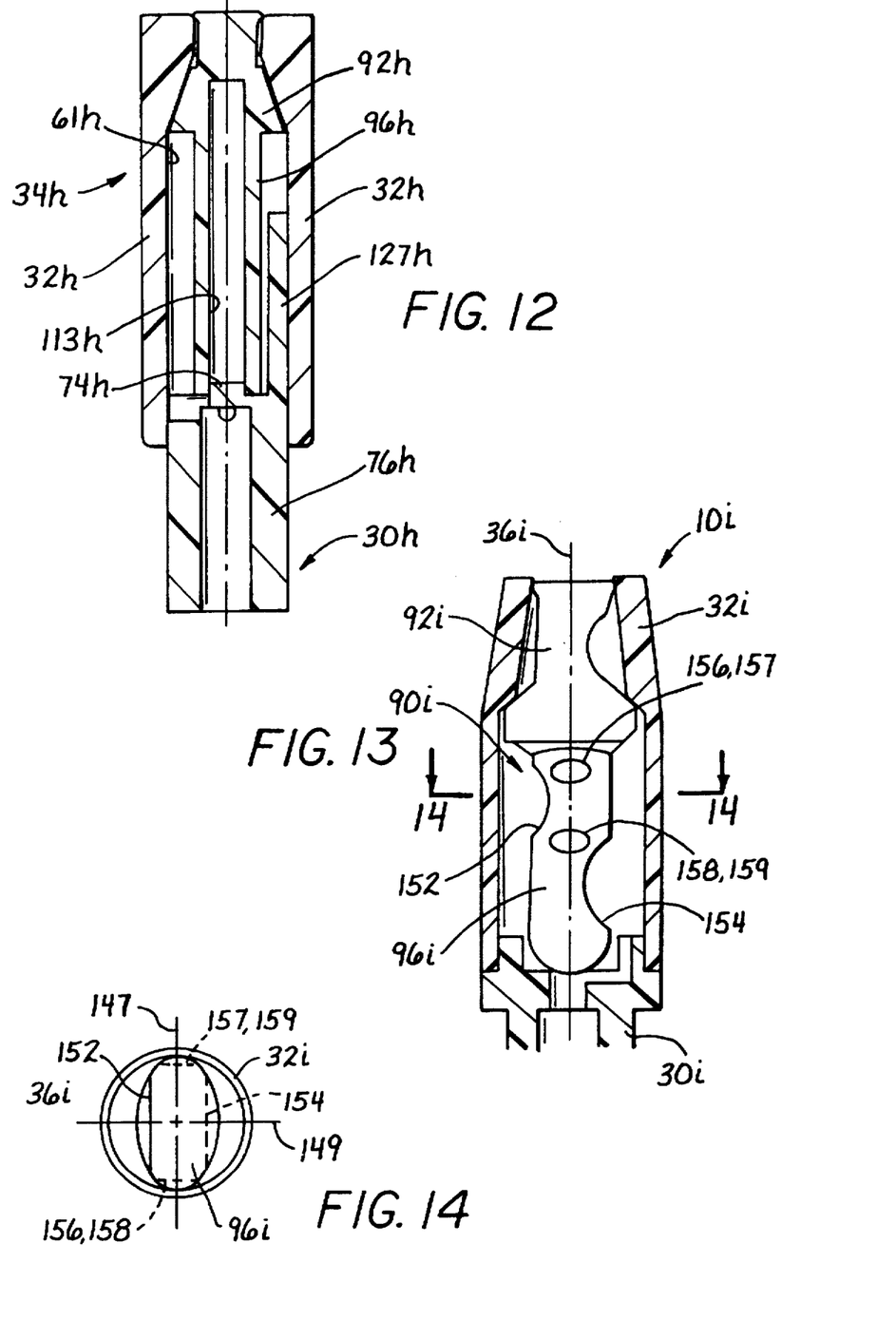

In still a further embodiment of the connector 10h illustrated in FIG. 12, the cap 32h fits directly over the base 30h. In this embodiment, the base 30h does not include the enlarged cylinder 74 (FIG. 2) but only the intermediate cylinder 76h which has substantially the same diameter as the inner surface 61h of the cap 32h. This embodiment of the connector 10h is of further interest due to its elongation of the bore 113h which is sized to fit on the post 74h. In this case, the bore 113h extends along the entire length of the shaft 96h and into the plug 92h. The post 74h will typically have an axial length significantly shorter than that of the bore 113h. As a consequence, those regions of the bore 113h which extend beyond the bore 74h provide the shaft 96h with a generally hollow structure. This configuration adds considerable flexibility to the shaft 96h and facilitates its canting or bending relationship with the housing 34h.

In still a further embodiment of the connector 10i illustrated in FIG. 13, the base 30i and cap 32i can be provided with any of the configurations previously disclosed. Similarly, the plug 92i can be formed as previously disclosed. This embodiment of FIG. 13 differs primarily in the structural formation of the shaft 96i which is provided with a generally sculpted configuration. As opposed to the previous embodiment where the shaft 96 has been formed substantially as a cylinder with a circular cross section, the shaft 96i of FIG. 13 can have generally any cross sectional shape such as the shape of an ellipse. This shape is best illustrated in FIG. 14 where the ellipse is characterized by a major axis 147 and a minor axis 149. Notches can be formed at various positions to provide a variety of advantages to the connector 10i. In the illustrated embodiment, these notches include a pair of relatively large notches 152 and 154 and a pair of relatively smaller notches 156 and 158. Opposing smaller notches 157 and 159, shown separately in FIG. 14, may be provided on the opposite side of the shaft 96i.

In the illustrated embodiment, the major notches 152 and 154 are formed on opposing sides of the elliptical shaft 96i. They are similar in shape but offset from each other along the axis 36i of the connector 10i. These notches 152 and 154 preferably extend parallel to the major axis 147 and inwardly toward the axis 36i a distance less than half of the dimension of the shaft 96i along the minor axis 149. In this embodiment, the smaller notches 156–159 are formed along the major axis 147.

The notches 152–159 are representative of any structural deviation in an otherwise smooth surface of the shaft 96i. The larger notches 152 and 154 will affect the canting or bending of the shaft 96a as it moves toward its compressed state. Where these notches 152 and 154 are formed at positions displaced along the axis 36i, the shaft 96i will tend to form a different bend at each of the notches 152 and 154. Where these notches 152, 154 are diametrically opposed, the bend of the shaft 96a will have an "s" shape as illustrated in FIG. 13. Thus the larger notches 152, 154 provide for more predictable bending of the shaft 96i in the compressed state. When the shaft 96i forms more than one bend, its axial length can generally be shorter. This advantage is particularly appreciated when a shorter connector 10i is desired.

The smaller notches 156–159 create flow channels around the valve element 90i. The smaller notches 156–159 also facilitate priming the connector 10i by preventing dead spots in the flow channel which might otherwise trap air bubbles.

In the illustrated embodiments, when the valve element 90 is in the natural closed state, its proximal surface 110 is in a substantially planar orientation with respect to the surface 47 of the cap 32. This orientation is preferred in order to avoid reservoirs and crevices which might otherwise result in pooling and bacterial contamination. With the substantially planar orientation of the surfaces 110 and 47, the proximal end of the connector 10 can be easily wiped in order to disinfect this region of the connector 10. This enables the connector 10 to be formed without the additional cost and inconvenience associated with a proximal end cap common to prior devices.

In each of the foregoing embodiments, the connector 10 functions to open and close the channel 63 by operation of the male Luer fitting 114. This type of fitting is commonly available and offers no risk of needle stick to the health care workers. The connector 10 can be constructed of only three elements including the cap 32 and base 30 which form the housing 34 and the elastomeric valve element 90. Both elongate and compact configurations can be provided depending on design considerations associated with the base 30 and the distal end of the shaft 96. The canting or bending of the valve element 90 can be facilitated by providing for an predetermined buckling section such as the notch 112 or by providing the finger 127 having an interfering relationship with the plug 92 as in the connector 10f. Both primary and secondary seals can be formed between the valve element 90 and the inner surface 61 of the cap 32. These seals can be non-simultaneously activated or deactivated to close or open the channel 63 of the connector 10.

In the foregoing embodiments, the connector 10 has been disclosed for use with intravenous tubing which is used to access the vascular system of a patient. The advantages provided by the connector would be equally appreciated if it were used to access other body conduits such as those associated with the urinary system. In general, the connector 10 will be operable by the male Luer fitting 114 to provide controlled access to the tubing set 12 or any other receptacle. Such other receptacles may include for example a catheter, a fluid reservoir or an injection manifold of the type commonly used for the administration of anesthesia. In this context, the connector 10 can be used to generally control the flow of any fluid, either gas or liquid, where it functions automatically to provide self-sealing with controlled access for either unidirectional or bidirectional flow.

Given these wide variations, which are all within the scope of this concept, one is cautioned not to restrict the invention to the embodiments which have been specifically disclosed and illustrated, but rather encouraged to determine the scope of the invention only with reference to the following claims.

We claim:

1. A connector adapted to facilitate bi-directional flow between a male Luer fitting and a receptacle tube, comprising:

a housing having an axis extending between a proximal end and a distal end, the housing having its distal end attached to the intravenous tube and portions defining a valve seat at its proximal end;

a valve element disposed in the housing and having a second axis, the valve element being movable by insertion of the male Luer fitting into the proximal end of the housing from a first position to a second position, the valve element in the first position forming with the valve seat of the housing a seal; and the valve element in the second position being disposed with the second axis of the valve element displaced from the first axis of the housing to form a fluid channel from the male Luer fitting to the receptacle tube.

2. The connector recited in claim 1 wherein:

the housing at its proximal end is defined by a first wipable surface; and the valve element has a second wipable surface which in the first position has a substantial planar relationship with the first wipable surface of the housing.

3. The connector recited in claim 1 wherein the fluid channel through the housing is disposed between the housing and the valve element.

4. The connector recited in claim 1 wherein the valve element is asymmetrical about the second axis so that a force directed against the valve element along the first axis of the housing causes the valve element to cant from the first position to the second position.

5. The connector recited in claim 4 wherein the second axis of the valve element is aligned with the first axis of the housing when the valve element is in the first position.

6. A connector adapted to facilitate bi-directional flow between a male Luer fitting and an intravenous tube, comprising:

a housing having an axis extending between a proximal end and a distal end, the housing having a proximal surface and a valve seat at its proximal end, and being adapted at its distal end for connection to the intravenous tube;

a valve element disposed in the housing and having a proximal surface, the valve element being movable by insertion of the male Luer fitting into the housing from a first position to a second position;

the valve element in the first position forming a seal with the valve seat of the housing;

the valve element in the second position being displaced off-axis from the first position to form a fluid channel from the male Luer fitting to the intravenous tube the fluid channel being non-concentric with the axis of the housing; and the proximal surface of the valve element having a substantially planar relationship with the proximal surface of the housing to facilitate antiseptic wiping at the proximal end of the connector.

7. The connector recited in claim 6 wherein:

the housing having a first axis;

the valve element has a second axis; and the valve element in the second position is disposed with the second axis in a displaced relationship with the first axis of the housing.

8. A connector adapted to facilitate access into a receptacle comprising:

a housing having a first axis extending between a proximal end and a distal end, the housing having its distal end attached to the receptacle; and a valve element disposed in the housing and defining with the housing a fluid channel extending between the proximal end and the distal end of the housing, the valve element having a second axis and being movable between a first position wherein the first axis is aligned with the second axis to close the fluid channel, and a second position wherein the second axis is displaced from the first axis to open the fluid channel.

9. The connector recited in claim 8 further comprising:

portions of the housing forming a valve seat; and the valve element being disposed in sealing engagement with the valve seat of the housing when the valve element is in the first position.

10. The connector recited in claim 9 further comprising:

portions of the valve element forming a predetermined area of buckling on one side of the second axis; whereby axial compression of the valve element collapses the valve element portions resulting in displacement of the second axis of the valve element from the first axis of the housing.

11. The connector recited in claim 10 wherein the valve element further comprises:

a plug;

a shaft disposed at the distal end of the housing and supporting the plug in proximity to the proximal end of the housing; and the portions of the valve element being included in the plug of the valve element.

12. The connector recited in claim 10 wherein the housing further comprises:

a base supporting the valve within the housing; and a cap coupled to the base and including the portions defining the valve seat.

13. The connector recited in claim 12 wherein the valve element further comprises:

a plug disposed along the second axis; and a shaft supporting the plug within the housing and disposed along a third axis different than the second axis.

14. The connector recited in claim 12 wherein the housing further comprises:

portions of the cap defining at least one longitudinal slot forming the channel in juxtaposition to the valve element.

15. A connector adapted to facilitate bi-directional flow with an intravenous tube, comprising:

a housing having an axis and a channel extending through the housing;

a base forming a portion of the housing;

a cap forming a portion of the housing and having a fixed relationship with the base;

a valve element disposed in the channel of the housing and defining with the housing a fluid flow path;

a plug included in the valve element;

a shaft included in the valve element and having properties for biasing the plug into sealing engagement with the housing to seal the channel in a first position of the valve element, and for being axially compressed to displace the plug from the housing and open the channel in a second position of the valve element; wherein the fluid flow path is concentric with the axis of the housing when the valve element is in the first position and the fluid flow path is displaced from the axis of the housing when the valve element is in the second position.

16. The connector recited in claim 15 further comprising:

portions of the base forming an arcuate cavity facing toward the cap of the housing; and portions of the shaft of the valve element having an arcuate configuration and being seated in the cavity of the base.

17. A method for operating a connector disposed between a male fitting and a receptacle, including the steps of:

providing a housing having a channel and an axis, the axis extending between a proximal end of the housing and a distal end of the housing;

positioning a valve element in the channel of the housing;

biasing the valve element to close the channel of the housing;

coupling the receptacle to the distal end of the housing;

engaging the valve element at the proximal end of the housing with a male fitting; and moving the male fitting generally parallel to the axis of the housing to open the channel substantially along only one side of the housing between the male fitting and the receptacle.

18. The method recited in claim 17 wherein the moving step includes the step of moving the male fitting generally along the axis of the housing.

19. The method recited in claim 17 wherein the method step includes the step of:

compressing the valve element to open the channel of the housing.

20. The method recited in claim 19 wherein:

the positioning step includes the step of providing a valve element with a length;

the biasing step includes the step of positioning the valve element with its length extending along the axis of the housing to close the channel; and the compressing step includes the step of compressing the valve element off-axis to open the channel of the housing between the male fitting and the receptacle.

21. A connector adapted to facilitate access into a receptacle, comprising:

a housing having an axis extending between a proximal end and a distal end, the housing having its distal end attached to the receptacle; and a valve element disposed in the housing and having a proximal surface, the valve element being movable between a first position wherein the proximal surface has a first acute angle with the axis of the housing and a second position wherein the proximal surface has a second angle with the axis of the housing; and the first angle being greater than the second angle.

22. The connector recited in claim 21 wherein:

the housing includes portions defining a channel extending through the housing;

the valve element being disposed within the channel of the housing;

the valve element in the first position forming a seal with the housing to close the channel; and the valve element in the second position being compressed off-axis to open the channel through the housing.

23. The connector recited in claim 21 wherein the valve element includes:

a plug disposed in proximity to the proximal end of the housing;

a shaft formed integral with the plug and extending into proximity with the distal end of the housing;

portions of the plug forming a first buckling section with characteristics for being axially compressed to move the proximal surface from the first position toward the second position; and portions of the shaft defining a second buckling section with characteristics for being compressed to move the proximal surface to the second position.

24. A connector adapted to facilitate access into a receptacle, comprising:

a housing having a first axis extending between a proximal end and a distal end, the housing having its distal end attached to the receptacle;

a valve element disposed in the housing and defining with the housing a fluid channel extending between the proximal end and the distal end of the housing, the valve element having a second axis and being movable between a first position wherein the first axis is aligned with the second axis to close the fluid channel, and a second position wherein the second axis is displaced from the first axis to open the fluid channel;

portions of the housing defining a valve seat, the valve element being disposed in sealing engagement with the valve seat of the housing when the valve element is in the first position;

portions of the valve element forming a predetermined area of buckling on one side of the second axis such that axial compression of the valve element collapses the valve element portions resulting in displacement of the second axis of the valve element from the first axis of the housing;

a base included in the housing and supporting the valve element within the housing;

a cap included in the housing and coupled to the base, the cap including the portions defining the valve seat; and a finger included in the base of the housing and extending longitudinally within the cap to engage the valve element between the first position of the valve element and the second position of the valve element in order to displace the second axis from the first axis.

* * * * *